United States Patent
Wickersheim et al.

(10) Patent No.: US 12,207,793 B2
(45) Date of Patent: Jan. 28, 2025

(54) COVER FOR AN ENDOSCOPE TIP AND ENDOSCOPE

(71) Applicant: SCHÖLLY FIBEROPTIC GMBH, Denzlingen (DE)

(72) Inventors: Johannes Wickersheim, Malterdingen (DE); Massimo Kubon, Emmendingen (DE); Jochen Dietrich, Elzach (DE); Mateusz Cichosz, Freiburg (DE)

(73) Assignee: SCHÖLLY FIBEROPTIC GMBH, Denzlingen (DE)

( * ) Notice: Subject to any disclaimer, the term of this patent is extended or adjusted under 35 U.S.C. 154(b) by 94 days.

(21) Appl. No.: 17/382,539

(22) Filed: Jul. 22, 2021

(65) Prior Publication Data
US 2022/0031150 A1    Feb. 3, 2022

(30) Foreign Application Priority Data
Jul. 30, 2020 (DE) .......... 102020120202.4

(51) Int. Cl.
*A61B 1/00* (2006.01)
*G02B 23/24* (2006.01)

(52) U.S. Cl.
CPC ...... *A61B 1/00137* (2013.01); *A61B 1/00096* (2013.01); *A61B 1/0011* (2013.01); *G02B 23/243* (2013.01)

(58) Field of Classification Search
CPC ............ A61B 1/00096; A61B 1/00101; A61B 1/00135; A61B 1/00137; A61B 1/00142; A61B 1/0607; A61B 1/0615

USPC .................................... 600/128, 129
See application file for complete search history.

(56) References Cited

U.S. PATENT DOCUMENTS

| | | | |
|---|---|---|---|
| 5,193,525 A | 3/1993 | Silverstein et al. | |
| 5,674,182 A | 10/1997 | Suzuki et al. | |
| 5,788,628 A * | 8/1998 | Matsuno ............... | A61B 1/015 600/125 |
| 9,398,839 B2 | 6/2016 | Rehe | |
| 2006/0183977 A1* | 8/2006 | Ishigami ............. | A61B 1/0684 600/179 |
| 2007/0249907 A1* | 10/2007 | Boulais .................. | A61B 5/064 600/179 |
| 2008/0021274 A1* | 1/2008 | Bayer ................ | A61B 1/00101 600/117 |
| 2008/0027276 A1* | 1/2008 | Rovegno ............ | G02B 23/2461 600/109 |
| 2013/0131447 A1* | 5/2013 | Benning .............. | A61B 1/0655 600/156 |

(Continued)

FOREIGN PATENT DOCUMENTS

| | | | | |
|---|---|---|---|---|
| DE | 202004021042 U1 | 9/2006 | | |
| WO | WO-2014158140 A1 * | 10/2014 | ......... | A61B 1/0011 |
| WO | WO-2021219379 A1 * | 11/2021 | ........ | A61B 1/00096 |

*Primary Examiner* — Aaron B Fairchild
*Assistant Examiner* — Stephen Floyd London
(74) *Attorney, Agent, or Firm* — Grogan, Tuccillo & Vanderleeden, LLP

(57) ABSTRACT

The invention relates to a cover for an endoscope tip, comprising at least one optical termination element and a shaft, the termination element comprising at least one light-guiding region and at least one image-guiding region, at least one optical barrier being formed between the at least one light-guiding region and the at least one image-guiding region by at least one separation element.

21 Claims, 2 Drawing Sheets

(56) References Cited

U.S. PATENT DOCUMENTS

Figure 1:
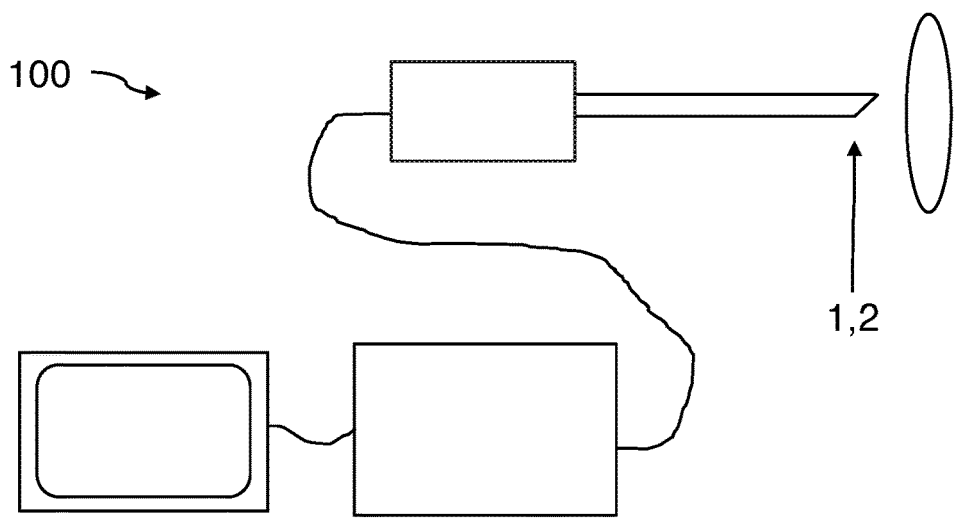

2016/0353983 A1* 12/2016 Onoe ................. A61B 1/00096
2020/0060520 A1*  2/2020 Sorensen ........... A61B 1/00096
2021/0228064 A1*  7/2021 Sorensen ........... G02B 23/2469

* cited by examiner

COVER FOR AN ENDOSCOPE TIP AND ENDOSCOPE

CROSS REFERENCE TO RELATED APPLICATIONS

This application claims priority to German Patent Application No. 102020120202.4, filed on Jul. 30, 2020, all of which is hereby incorporated by reference in its entirety.

BACKGROUND

The invention relates to a cover, more particularly a disposable sterile cover, for an endoscope tip, comprising at least one termination element and a shaft, the termination element having at least one light-guiding region and at least one image-guiding region.

Covers of the aforementioned type are already used for endoscopes, such as, e.g., laparoscopes, for the purposes of being pulled over an endoscope tip. Consequently, covers embodied as disposable sterile covers in particular, which are pulled on devices, allow the device to be used for surgical interventions without preparation such as, e.g., sterilization. Further, this facilitates a longer service life of the device and moreover prevents a great loss of time until the next application by avoiding preparation.

In previously utilized covers of the aforementioned type, a conventional optical flat is generally arranged at a distal end of the cover as a termination element. However, a potential disadvantage thereof is that reflections may arise in the image transmission as a result of crosstalk of light signals from the light-guiding region into the image-guiding region. These "standing" reflections and/or the stray light are permanent and therefore perceived as bothersome to impeding by the surgeon and ultimately unacceptable. In particular, these standing reflections occur in novel solid-state light sources, which preferably have a large illumination angle of greater than 60°-80° (cf. optical fibers) (for example, LEDs>120°). As a result, very small input angles arise in the outer region of the illumination and toward the cover glass, as a result of which, light is easily coupled into the cover glass and transmitted laterally to the image region.

Therefore, there is a need for a cover of the type set forth at the outset, in which no such bothersome reflections occur during an operation.

SUMMARY

In particular, a cover of the type set forth at the outset is proposed according to embodiments of the invention, the cover being characterized in that at least one light-guiding region and at least one image-guiding region are optically decoupled from one another by way of at least one separation element. Consequently, the at least one separation element can prevent crosstalk of light signals from the light-guiding region into the image-guiding region, and so no bothersome reflections are visible to a user. Consequently, the image transmission is significantly improved in relation to known devices.

Advantageous configurations of embodiments of the invention are described below, which can optionally be combined individually or in combination with the features of other configurations together with the features as claimed.

In one embodiment, the cover can have at least two image-guiding regions, each of the image-guiding regions being optically separated from at least one image-guiding region by at least one separation element or by at least one separation element in each case. By way of example, a plurality of image-guiding regions allow three-dimensional images to be recorded.

According to an advantageous development, the termination element can be embodied as a termination glass. The termination element can particularly preferably be embodied as an optical flat.

According to one advantageous development, in certain embodiments, provision can be made for the at least one image-guiding region and/or the at least one light-guiding region to be completely sealed off by the at least one separation element. As an alternative, or in addition thereto, the at least one separation element can be continuous in a circumferential direction. Consequently, the at least one separation element defines regions that are completely separated from one another in order to better prevent crosstalk of light signals between the regions.

According to an embodiment, the at least one image-guiding region and the at least one light-guiding region may be interconnected. Preferably, there can be a connecting section, shielded by the at least one separation element, between the at least one image-guiding region and the at least one light-guiding region. As an alternative, or in addition thereto, the at least one separation element may be interrupted in a circumferential direction. This is advantageous in that it allows a simpler and more cost-effective manufacture of a transparent region which comprises at least the light-guiding region and the image-guiding region. By way of example, the light-guiding region and the image-guiding region can be produced in one piece by, for example, injection molding.

To be able to prevent an emission from the light-guiding region into the image-guiding region even better, the at least one separation element may be produced from a nontransparent material, such as a light-absorbing or light-reflecting material.

According to a further embodiment of the cover, the cover comprises a plurality of separation elements. In particular, the cover can comprise a plurality of at least partly overlapping separation elements. As an alternative, or in addition thereto, provision can be made for different separation elements to be assigned to the at least one light-guiding region and to the at least one image-guiding region. Consequently, crosstalk of light signals from the light-guiding region into the image-guiding region can be prevented even better.

According to a further embodiment, the at least one separation element may have a varying strength in the longitudinal direction. Preferably, the at least one separation element can have a conical embodiment in the longitudinal direction. A resultant inclination of the separation element allows the latter to be matched to a beam path of the imaging region in order to avoid vignetting. Consequently, the image quality of the image-guiding region can be improved.

According to an embodiment, the at least one separation element may extend continuously in the longitudinal direction and/or from an inner side to an outer side of the at least one termination element. Consequently, a particularly good optical barrier can be formed by the separation element.

According to a further embodiment, the at least one separation element and the shaft may be interconnected, in particular frictionally connected and/or integrally joined. As an alternative and/or in addition thereto, provision can be made for the at least one separation element and the shaft to be produced from the same material, preferably as one piece. In particular, the separation element and/or the shaft can be produced by injection molding, preferably by two-component injection molding. To be able to achieve simple and cost-effective fastening of the termination element, provision can further preferably be made for the at least one termination element to be at least partially insert molded in nontransparent material.

According to one embodiment of the cover, the at least one separation ring may be formed by the at least one separation element. Preferably, at least one open and/or at least one closed separation ring can be formed by the at least one separation element. Consequently, a particularly good optical barrier and/or a stray light trap is formed between the regions.

According to one embodiment, the cover may have at least two light-guiding regions and/or only one image-guiding region. Preferably, the at least one image-guiding region can be formed between the at least two light-guiding regions or within a light-guiding region that surrounds the image-guiding region. Consequently, reflections can be prevented particularly well.

According to a further embodiment, a transparent region, in particular made of at least one light-guiding region and the at least one image-guiding region, to completely surround the at least one separation element. Preferably, the transparent region of the cover is formed in one piece, reducing the manufacturing costs.

According to a further embodiment, a transparent region, for example the aforementioned transparent region, may overlap a nontransparent region, the latter in particular comprising the at least one separation element and/or the shaft, in the distal direction. What this can easily achieve is that, firstly, fastening the transparent region to the nontransparent region is attainable and, secondly, a light cone defined by the image recording apparatus behind the surface is curtailed as little as possible.

According to a further embodiment, the cover, in particular the termination element and/or a nontransparent region or the nontransparent region, may have at least one light source cutout, through which the illumination light of an endoscope can emerge. In particular, the light of the light source, which may be situated in the distal region of an endoscope, can be emitted through the light source cutout for the purposes of illuminating the field of view.

According to an embodiment, a perpendicular angle of incidence into the termination element may be an angle to a longitudinal axis of the shaft. In this case, provision can be made for a distal end of the cover embodied in angled fashion to have a cut off acute angle in order to avoid dead zones that are unwanted from an injection molding point of view.

According to an embodiment, provision can be made for a transparent connecting section, for example the aforementioned transparent connecting section, between the at least one light-guiding region and the at least one image-guiding region to have at least one change of direction, preferably at least two changes of direction. This can achieve an advantage of simplified manufacture by virtue of the transparent region preferably having a one-piece embodiment and, moreover, it also being possible to set up a good optical barrier between the regions in order to avoid crosstalk.

According to an embodiment, the cover may have at least one connecting site between the nontransparent region and the transparent region. Preferably, the termination element can have at least one coupling site and the shaft can have a counter coupling site corresponding thereto, said coupling sites being able to be interconnected or being interconnected. This allows simple manufacture of the cover. In particular, a frictional connection and/or an integral joint can be formed by the connecting site.

According to a further embodiment, the at least one light-guiding region and the at least one image-guiding region may have different optical qualities. In particular, at least one of the regions can have at least one lens, for example at least one lens selected from converging lens, diffuser lens, aspherical lens, Fresnel lens structure. Particularly preferably, the at least one light-guiding region can be subdivided into at least two portions with different optical qualities.

The invention further relates to an endoscope having a cover as described and/or claimed herein, in particular wherein the cover is able to be placed or is placed on an endoscope tip of the endoscope that is sealed to the outside.

The invention will now be explained in more detail on the basis of a plurality of exemplary embodiments without however being restricted to these exemplary embodiments. Further exemplary embodiments arise by combining the features of individual claims or of a plurality of claims among themselves and/or with individual features or a plurality of features of the exemplary embodiments.

DRAWINGS

Figure 2:
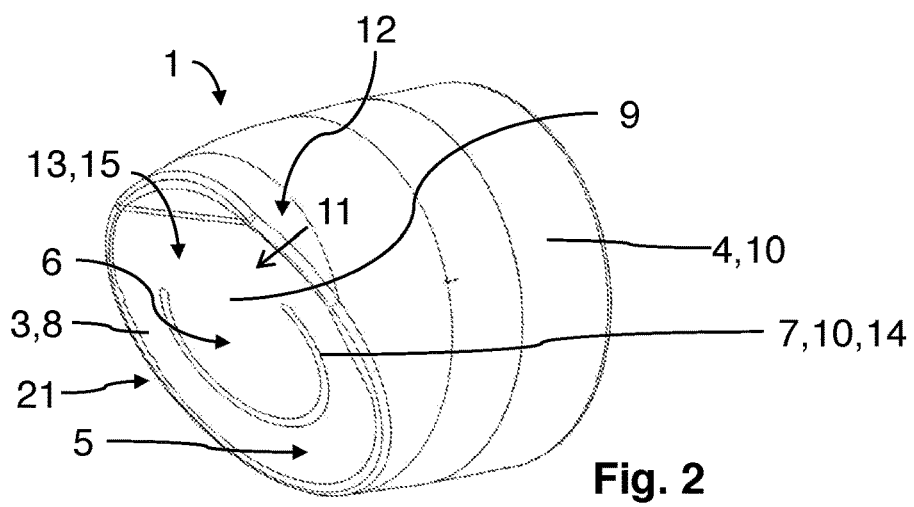
Figure 3:
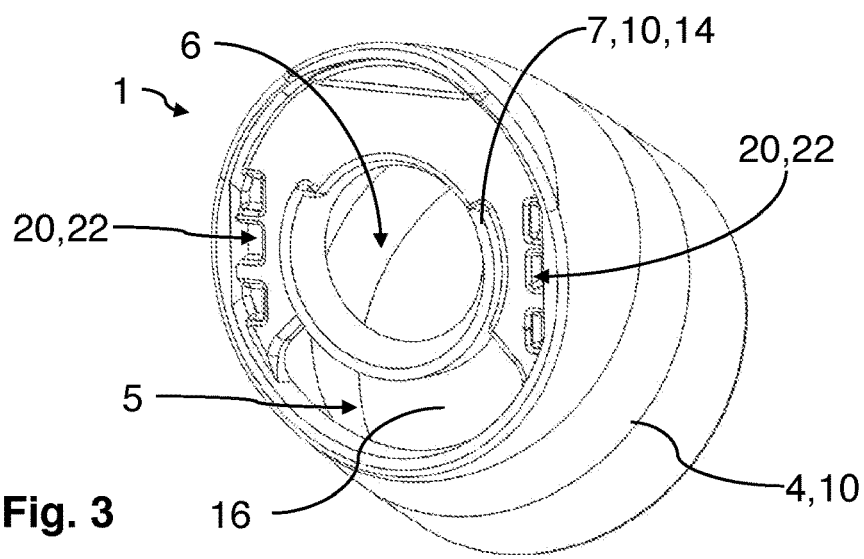
Figure 4:
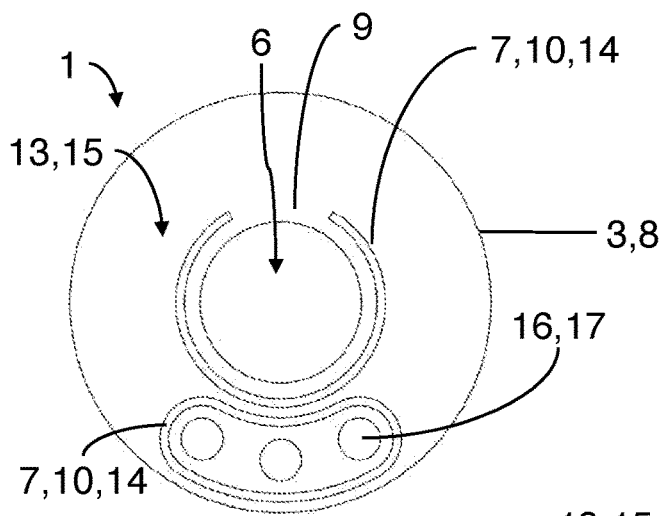
Figure 5:
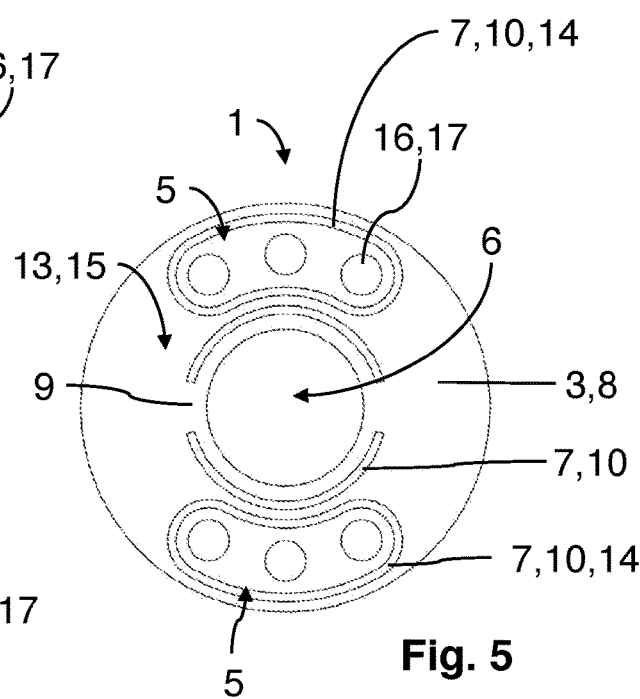
Figure 6:
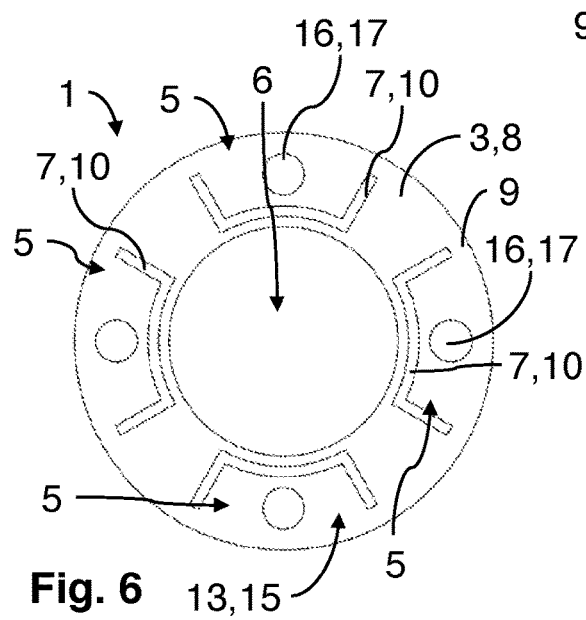
Figure 7:
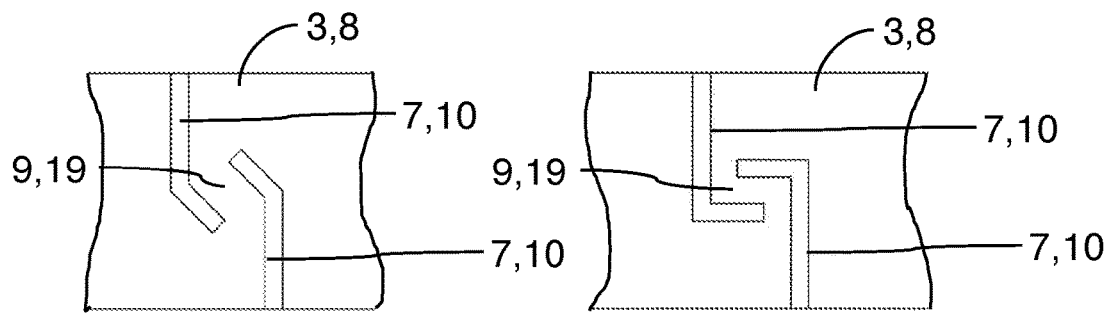

In detail:

FIG. 1 shows an overall view of an endoscopy system comprising an endoscope, a cover according to an embodiment of the invention having been placed on the distal endoscope tip thereof, FIG. 2 shows a perspective view of a possible configuration of a cover according to an embodiment of the invention, comprising a shaft which has a termination element arranged at the distal end thereof, FIG. 3 shows the configuration of FIG. 2 where the termination element has been removed, FIG. 4 shows a further possible embodiment variant of a cover according to the invention, with a light-guiding region and an image-guiding region, FIG. 5 shows a further possible embodiment variant of a cover according to the invention, with two light-guiding regions and an image-guiding region, FIG. 6 shows a further possible embodiment variant of a cover according to the invention, with four light-guiding regions and an image-guiding region, and FIG. 7 shows cross sections of two possible configurations of the connecting section in the region of the separation element.

FIGS. 1-6 illustrate possible embodiment variants of a cover which is in each case denoted by 1 as a whole.

DETAILED DESCRIPTION

By way of example, the cover 1 can be configured as a disposable sterile cover.

The cover 1 is set up to be placed on an endoscope tip 2 of an endoscope 100, such as a laparoscope for example. This can lengthen the service life of the endoscope overall since less material wear occurs. Moreover, this allows a lengthy preparation of the endoscope 1 to be dispensed with since, for reuse, only the cover 1 need be replaced in order to allow use of the endoscope 100 on the patient again.

According to an embodiment of the invention, the cover 1 includes at least one termination element 3 and a shaft 4. The termination element 3, which forms a transparent region 15 (optical region) of the cover has at least one light-guiding region 5 and at least one image-guiding region 6. Below, different configuration options for the transparent region 15 are described in detail. Provision can also be made for two or more than two image-guiding regions 6 to be formed, for example in order to be able to create three-dimensional recordings.

The at least one light-guiding region 5 and the at least one image-guiding region 6 are optically decoupled from one another by at least one separation element 7, which forms an optical barrier between the regions 5, 6. Consequently, no light signals, particularly in the form of reflections, can crosstalk from the light-guiding region 5 to the image-guiding region 6. Such reflections impair the image recording of an endoscope 100 via the image-guiding region 6 and should therefore be avoided as a matter of principle.

Consequently, at least one stray light trap can be formed by the at least one separation element 7.

In the embodiments shown in FIGS. 2, 4, 5 and 6, the termination element 3 is embodied as an optical flat 8 in each case, the optical flat 8 forming a distal termination of the cover 1. The opposite side of the shaft 4 has an opening, by way of which it is possible to insert the endoscope tip 2 into the cover 1. Consequently, the cover 1 has a receptacle for the endoscope tip 2, into which it is possible to at least partly insert said endoscope tip 2.

FIGS. 4 and 5 each show embodiment variants whose light-guiding regions 5 are completely enclosed by a separation element 7.

FIGS. 2 and 6 each show embodiment variants in which the at least one separation element 7 (in this case the four separation elements 7) does not completely enclose the respective light-guiding region 5 such that the light-guiding region 5 is connected to the image-guiding region 6 via at least one connecting section 9.

The at least one separation element 7 and/or the shaft 4 is/are formed from a nontransparent material 10. By way of example, the nontransparent material 10 can be a light-absorbing or light-reflecting material. Consequently, it is possible to establish a particularly good optical barrier between the light-guiding region(s) 5 and the image-guiding region 6.

FIGS. 4-7 show embodiment variants of a cover 1, in each case with a plurality of separation elements 7.

FIG. 7 shows two possible configurations of a connecting section 9 in detail, the light-guiding region 5 and the image-guiding region 6 being connected thereby. The separation elements 7 overlap in such a way at the connecting region 9 that they form an optical barrier between the light-guiding region 5 and the image-guiding region 6, in particular in such a way that no light reflections reach the image-guiding region from the light-guiding region 5. Consequently, the connecting section 9 has at least one change of direction 19.

The separation elements 7 can have different shapes and/or arrangements at the termination element 3. Examples of possible configurations are illustrated in FIGS. 4-6. Here, provision can be made for the termination element 3 to have a symmetric configuration, for example. Preferably, the termination element can have mirror symmetry and/or rotational symmetry, more particularly discontinuous rotational symmetry. Consequently, this facilitates a particularly good illumination and, at the same time, particularly good image recording.

The termination element 3 of FIG. 4 has a first separation element 7 configured as an open separation ring 14, which partly encloses the image-guiding region 6 with the exception of an opening facing away from the light-guiding region 5. Moreover, the termination element 3 of FIG. 4 comprises a second separation element 7, which is embodied as a closed separation ring 14 that completely encloses the light-guiding region 5.

The termination element 3 of FIG. 5 has an image-guiding region 6 and two light-guiding regions 5, which are each completely enclosed by a separation element 7 which is assigned to the respective light-guiding region 5 and embodied as a separation ring 14.

The image-guiding region 5 is shielded from each of the light-guiding regions 5 by a separation element 7 in each case. Two separation elements 7 are consequently arranged in each case between each light-guiding region 5 and the image-guiding region 6 and consequently form a twofold optical barrier, which prevents crosstalk particularly well.

The termination element 3 of FIG. 6 has an image-guiding region 6 and four light-guiding regions 5. The light-guiding regions 5 are arranged around the image-guiding region 6 in a manner spaced apart from one another, in particular with the same distance from one another, in the circumferential direction. Each light-guiding region 5 is optically decoupled from the image-guiding region 6 by way of a separation element 7 assigned thereto in each case, by virtue of the respective separation element 7 forming an optical barrier between the light-guiding region 5 and the centrally arranged image-guiding region 6.

The at least one separation element 7 can extend in the longitudinal direction 11, in particular from an inner side 12 to an outer side 13 of the termination element 3, and can have a changing width (radial extent) in the process.

The at least one separation element 7 and the shaft 4 are interconnected. The at least one separation element 7 and the shaft 4 can be produced from the same material, preferably as one piece. By way of example, the production of the cover 1 can be implemented at least in part by injection molding, preferably by two-component injection molding. The at least one termination element 3 can be insert molded in nontransparent material 10 and can consequently be affixed to the shaft 4.

The cover 1 has at least one light source cutout 16, through which the light of the light source 17, which may be situated at the distal region of the endoscope 100, can be emitted for the purposes of illuminating the field of view. The at least one light source cutout 16 is located within a light-guiding region 5.

FIG. 2 shows an embodiment variant in which the termination element 3, in particular perpendicular input angle of light into the termination element 3, is angled in relation to the longitudinal axis of the shaft 4 in such a way that the angle is greater than or less than 90 degrees.

FIG. 3 shows an embodiment variant of the cover 1 with a connecting site 20 (without termination element 3). The connecting site 20 can comprise a coupling site 21 of the termination element 3 (indicated in FIG. 2) and a counter coupling site 22, fitting thereto, of the shaft 4, said coupling sites being interconnected in an assembly position. By way of example, the connecting site 20 can be embodied as a latching connection.

By way of example, the at least one separation element 7 can be produced by filling a recess in the termination element 3 with optically tight adhesive mass.

As an alternative or in addition thereto, the at least one separation element 7 can be produced by local laser engraving into glass and/or polymers, in particular in order to obtain a light-diffuse layer.

As a further alternative or as a further addition, the at least one separation element 7 can be produced by one sided or two-sided local etching of glass and/or polymers in order to create a material transition that is difficult for stray light to overcome.

Thus, in particular, the invention relates to a cover 1, in particular a disposable sterile cover, for an endoscope tip 2, comprising at least one optical termination element 3 and a shaft 4, the termination element 3 comprising at least one light-guiding region 5 and at least one image-guiding region 6, at least one optical barrier being formed between the at least one light-guiding region 5 and the at least one image-guiding region 6 by at least one separation element 7.

What is claimed is:

1. A cover for an endoscope tip comprising:
   at least one termination element and a shaft, the at least one termination element having at least one light-guiding region and at least one image-guiding region,
   wherein the at least one light-guiding region and the at least one image-guiding region are optically decoupled from one another by way of at least two separation elements,
   wherein the cover is configured for placement on the endoscope tip of an endoscope that is sealed to an outside;
   wherein a connecting section between the at least one light-guiding region and the at least one image-guiding region has at least one change of direction, the at least one change of direction of the connecting section is located between the at least two separation elements;
   wherein the at least two separation elements overlap at the connecting section creating the at least one change of direction and forming an optical barrier between the at least one light-guiding region and the at least one image-guiding region, the at least two separation elements having a substantially symmetrical shape at the overlap.

2. The cover as claimed in claim 1, wherein the at least one termination element comprises a termination glass.

3. The cover as claimed in claim 1, wherein the at least one image-guiding region and/or the at least one light-guiding region are shielded by at least one separation element of the at least two separation elements.

4. The cover as claimed in claim 1, wherein the at least one image-guiding region and the at least one light-guiding region are interconnected.

5. The cover as claimed in claim 1, wherein at least one separation element of the at least two separation elements is produced from a nontransparent material.

6. The cover as claimed in claim 5 wherein the nontransparent material is a light-absorbing or light-reflecting material.

7. The cover as claimed in claim 1, wherein at least one separation element of the at least two separation elements comprises a plurality of at least partly overlapping separation elements, with different separation elements being assigned to the at least one light-guiding region and to the at least one image-guiding region.

8. The cover as claimed in claim 1, wherein at least one separation element of the at least two separation elements has a conical configuration in a longitudinal direction which leads to a varying strength in a longitudinal direction.

9. The cover as claimed in claim 1, wherein at least one separation element of the at least two separation elements extends continuously in a longitudinal direction from an inner side to an outer side of the at least one termination element.

10. The cover as claimed in claim 1, wherein at least one separation element of the at least two separation elements and the shaft are interconnected and/or wherein at least one separation element of the at least two separation elements and the shaft are produced from a same material by two-component injection molding, and the at least one termination element is insert molded in a nontransparent material.

11. The cover as claimed in claim 1, wherein at least one closed separation ring is formed by at least one separation element of the at least two separation elements.

12. The cover as claimed in claim 1, wherein the at least one light-guiding region comprises at least two light-guiding regions, and the at least one image-guiding region being formed between the at least two light-guiding regions or within one of the at least two light-guiding regions that surround the at least one image-guiding region.

13. The cover as claimed in claim 1, wherein a transparent region, made of the at least one light-guiding region and the at least one image-guiding region, completely surrounds at least one separation element of the at least two separation elements.

14. The cover as claimed in claim 1, wherein a transparent region overlaps a nontransparent region, the latter comprising at least one separation element of the at least two separation elements and/or the shaft, in a distal direction.

15. The cover as claimed in claim 1, wherein the at least one termination element and/or a nontransparent region has at least one light source cutout, through which an illumination light of an endoscope can emerge.

16. The cover as claimed in claim 1, wherein a perpendicular angle of incidence into the at least one termination element is at an angle perpendicular to a longitudinal axis of the shaft.

17. The cover as claimed in claim 1, wherein the cover has at least one connecting site between a nontransparent region and a transparent region.

18. The cover as claimed in claim 1, wherein the at least one light-guiding region and the at least one image-guiding region have different optical qualities, wherein at least one of the regions has at least one lens selected from a converging lens, diffuser lens, aspherical lens, of Fresnel lens structure.

19. The cover as claimed in claim 1, wherein the at least one light-guiding region is subdivided into at least two portions with different optical qualities.

20. The cover of claim 1 wherein the at least one termination element comprises an optical flat.

21. The cover of claim 1 having at least one coupling site and the shaft having a counter coupling site corresponding thereto, said coupling sites being able to be interconnected.

* * * * *